United States Patent

Kido et al.

[11] Patent Number: 5,840,992
[45] Date of Patent: Nov. 24, 1998

[54] PROCESS FOR PRODUCING 6-METHYLHEPTAN-2-ONE

[75] Inventors: Yoichi Kido; Masahiko Kitayama; Koichi Yoneda; Hideharu Iwasaki; Takashi Onishi, all of Ibaraki, Japan

[73] Assignee: Kuraray Co., Ltd., Kurashiki, Japan

[21] Appl. No.: 737,926

[22] PCT Filed: Apr. 1, 1996

[86] PCT No.: PCT/JP96/00881

§ 371 Date: Dec. 2, 1996

§ 102(e) Date: Dec. 2, 1996

[87] PCT Pub. No.: WO96/31454

PCT Pub. Date: Oct. 10, 1996

[30] Foreign Application Priority Data

Apr. 4, 1995 [JP] Japan .................................. 7-103143

[51] Int. Cl.⁶ .................................................. C07C 45/42
[52] U.S. Cl. .......................................... 568/392; 568/390
[58] Field of Search ....................... 568/392, 390

[56] References Cited

U.S. PATENT DOCUMENTS

| | | | |
|---|---|---|---|
| 2,088,018 | 7/1937 | Wickert et al. | 568/390 |
| 3,824,272 | 7/1974 | Brossi et al. | 568/390 |
| 4,146,581 | 3/1979 | Nissen et al. | 568/390 |
| 4,329,657 | 5/1982 | Nissen et al. | 568/390 |
| 5,132,464 | 7/1992 | Rossiter et al. | 568/396 |
| 5,300,654 | 4/1994 | Nikajima et al. | 568/390 |
| 5,583,263 | 12/1996 | Muthusamy et al. | 568/392 |

FOREIGN PATENT DOCUMENTS 26 25 541  12/1977  Germany .
28 39 474   3/1980  Germany .

OTHER PUBLICATIONS

*R. T. Morrison, et al.*, Verlag Chemie GmbH, pp. 768–773, 1978, "Lehrbuch Der Organischen Chemie".

*Jerry March*, John Wiley & Sons, pp. 937–939, 1992, "Advanced Organic Chemistry".

*Primary Examiner*—James H. Reamer
*Attorney, Agent, or Firm*—Oblon, Spivak, McClelland, Maier & Neustadt, P.C.

[57] ABSTRACT

In order to make it possible to produce 6-methylheptan-2-one, which is useful as a material for synthesizing isophytol or as a material for synthesizing fragrances such as tetrahydrolinalool and dihydrogeraniol, efficiently and in an industrially simple manner, isovaleral and acetone are subjected to aldol condensation in the presence of a basic substance to form a condensate which contains 4-hydroxy-6-methylheptan-2-one, and then the condensate is subjected to hydrogenation reaction under a dehydration condition to obtain the 6-methylheptan-2-one.

12 Claims, No Drawings

PROCESS FOR PRODUCING 6-METHYLHEPTAN-2-ONE

TECHNICAL FIELD

This invention relates to a novel process for producing 6-methylheptan-2-one, which is useful as a material for synthesizing isophytol [see J. Org. Chem., 32, 177 (1967) and J. Org. Chem., 28, 45 (1963)] or as a material for synthesizing fragrances such as tetrahydrolinalool and dihydrogeraniol [see Bull. Soc. Chim. Fr., 1586 (1955)].

BACKGROUND ART

As processes for producing 6-methylheptan-2-one, processes (i) to (iv) shown below are known in the art.

(i) A process in which an isoamyl halide and an acetoacetic acid ester are subjected to condensation in the presence of a base, followed by hydrolysis and decarboxylation reaction (see, e.g., "SYNTHETIC ORGANIC CHEMISTRY", p.327, written by Wagner, John Wiley & Sons, Inc.);

(ii) a process in which 6-methyl-5-hepten-2-one or 6-methyl-3,5-heptadien-2-one is subjected to a hydrogenation reaction in the presence of a catalyst such as Ni [see, e.g., Izv. Akad. Nauk SSSR, Ser. Knim. (5), 1052 (1972)];

(iii) a process in which 6-methyl-5-hepten-2-ol is treated with a mixture of 85% phosphoric acid and phosphorus pentoxide [see, Bull. Soc. Chim. Fr., 1799 (1963)]; and (iv) a process in which isovaleral and acetone are allowed to react with each other in a stream of hydrogen, in the presence of a catalyst containing nickel and/or cobalt and zinc oxide or the like as main components (Japanese Patent Application Laid-open No. 53-22186).

The above processes, however, have problems as discussed below. That is, in the case of the process (i), there are the problems that the starting material (acetoacetic acid ester) is expensive and also the process requires for the condensation the base at least in an equimolar amount with respect to the acetoacetic acid ester, resulting in a high cost for the production of the 6-methylheptan-2-one. In the case of the process (ii), there is the problem that the production of the starting material (6-methyl-5-hepten-2-one or 6-methyl-3,5-heptadien-2-one) itself is complicated. In the case of the process (iii), there are the problems that not only the production of 6-methylhepten-2-ol itself is complicated, but also 85% phosphoric acid and phosphorus pentoxide are used in a large quantity to require much labor for the disposal of waste water. In the case of the process (iv), there is the problem that the reaction must be carried out at high temperatures and under a liquid phase condition, so that it requires special production apparatus.

Thus, although some methods as above are known for the production of 6-methylheptan-2-one, all the methods have subjects to be settled in respect of starting material costs and production apparatus. Under the existing circumstances, no industrially advantageous process has been established for producing 6-methylheptan-2-one.

Objects of the present invention are to solve the problems involved in the prior art discussed above and to provide an industrially advantageous process for producing 6-methylheptan-2-one.

DISCLOSURE OF THE INVENTION

The present inventors have discovered that 6-methylheptan-2-one can be produced efficiently and in an industrially simple manner when isovaleral and acetone, which are produced in an industrial scale and available inexpensively, are used as starting materials and when these are subjected to aldol condensation and the resulting condensate is subjected to hydrogenation under a dehydration condition, and have accomplished the present invention.

More specifically, the present invention provides a process for producing 6-methylheptan-2-one, comprising subjecting isovaleral and acetone to aldol condensation in the presence of a basic substance to form a condensate which contains 4-hydroxy-6-methylheptan-2-one, and subjecting the condensate to hydrogenation reaction under a dehydration condition.

In the present invention, the "condensate which contains 4-hydroxy-6-methylheptan-2-one" refers to a single compound of 4-hydroxy-6-methylheptan-2-one, or a mixture of this compound with at least one compound selected from the group consisting of 6-methyl-3-hepten-2-one, 6-methyl-4-hepten-2-one and 6-methyl-5-hepten-2-one. Hereinafter, unless particularly noted, the "condensate which contains 4-hydroxy-6-methylheptan-2-one" is simply called "4-hydroxy-6-methylheptan-2-one-containing condensate".

BEST MODE FOR WORKING THE INVENTION

The present invention is described below in detail.

In the process for producing 6-methylheptan-2-one of the present invention, first isovaleral and acetone are allowed to react with each other to obtain a 4-hydroxy-6-methylheptan-2-one-containing condensate.

Here, from the viewpoint of improving reaction selectivity on the basis of more expensive isovaleral so that the 4-hydroxy-6-methylheptan-2-one-containing condensate can be synthesized in a good efficiency, isovaleral and acetone may be used in an isovaleral/acetone molar ratio usually ranging from 1/3 to 1/10, and preferably from 1/5 to 1/8.

The aldol condensation of isovaleral with acetone is carried out in the presence of a basic substance. Such a basic substance may preferably include, e.g., alkali metal hydroxides such as sodium hydroxide and potassium hydroxide, and alkaline-earth metal hydroxides such as barium hydroxide and calcium hydroxide. Any of these may be used in the form of a solid or an aqueous solution at a concentration of from 1 to 50%. Any of these compounds may be used alone or in combination of two or more kinds.

As the basic substance, besides these, it is also possible to use metal alkoxides such as sodium methoxide, potassium methoxide, sodium t-butoxide, and potassium t-butoxide, and metal amides such as lithium diisopropylamide (LDA) and lithium bistrimethylsilylamide (LHMDS).

Any of these basic substances may be used usually in an amount of from 0.1 to 20 mol % based on isovaleral, and, taking account of reaction rate and cost of production, preferably in an amount ranging from 0.5 to 5 mol %.

The aldol condensation may be usually carried out at a temperature ranging from −20° C. to 100° C. In order to control the reaction rate at a practical level and also to inhibit the formation of a compound with high boiling temperature by side reaction to improve selectivity to the 4-hydroxy-6-methylheptan-2-one-containing condensate, it may preferably be carried out at a temperature ranging from 30° C. to 60° C. The reaction time may vary depending on reaction conditions, and usually may be in the range of from 10 minutes to 10 hours. For example, when an aqueous 5% sodium hydroxide is used as the basic substance in an amount of 1 mol % based on isovaleral and the aldol condensation is carried out at a temperature of about 40° C., the aldol condensation is completed in about 30 minutes.

In the present invention, the aldol condensation may be carried out batchwise, or may be continuously carried out in such a way that a mixture of isovaleral and acetone is continuously fed together with the basic substance to a reactor kept at a predetermined temperature and the resulting mixture is continuously drawn out after a predetermined residence time.

When the aldol condensation is carried out, it is not necessarily required to use a solvent. From the viewpoint of volume efficiency, the reaction may preferably be carried out without a solvent. However, from the viewpoint of the control of reaction, a solvent inert to the aldol condensation may be used. Such a solvent may include, e.g., lower aliphatic alcohols such as methanol, ethanol, propanol, isopropanol, butanol, s-butanol and t-butanol; cyclic or acyclic ethers such as tetrahydrofuran, 1,4-dioxane, diethyl ether, diisopropyl ether and di-n-butyl ether; and aliphatic or aromatic hydrocarbons such as hexane, heptane, octane, benzene, toluene and xylene.

From the reaction solution obtained as a result of the aldol condensation as described above (hereinafter, this reaction solution is simply called "aldol reaction solution"), the 4-hydroxy-6-methylheptan-2-one-containing condensate can be separated and obtained by subjecting the aldol reaction solution to neutralization with an acidic substance such as acetic acid, followed by purification through distillation. In the 4-hydroxy-6-methylheptan-2-one-containing condensate obtained, 20 to 90% by weight of 4-hydroxy-6-methylheptan-2-one and 5 to 75% by weight of 6-methyl-3-hepten-2-one are usually contained, which are variable depending on reaction conditions and distillation conditions.

Next, in the present invention, the 4-hydroxy-6-methylheptan-2-one-containing condensate is subjected to hydrogenation reaction under a dehydration condition to obtain the 6-methylheptan-2-one.

Here, as the 4-hydroxy-6-methylheptan-2-one-containing condensate used as a starting material at the time of hydrogenation reaction, the one separated and obtained by the purification through distillation as described above may be used. If necessary, the aldol reaction solution may be used as it is. Alternatively, a residue obtained after unreacted materials used in excess has been collected from the aldol reaction solution by distillation may be used, or a fraction, which is obtained from the residue by simple evaporation to remove any high-boiling materials and salts formed at the time of neutralization, may be used.

In the present invention, the hydrogenation reaction is carried out under a dehydration condition. The reason therefor is as follows: If the condensate is merely hydrogenated, the 6-methyl-3-hepten-2-one which is contained only in an amount of 5 to 75% by weight in the 4-hydroxy-6-methylheptan-2-one-containing condensate can only be converted into the desired 6-methylheptan-2-one, whereas the 4-hydroxy-6-methylheptan-2-one which is contained in an amount of 20 to 90% by weight is not utilized at all. The hydrogenation reaction carried out under a dehydration condition makes it possible to convert the 4-hydroxy-6-methylheptan-2-one into 6-methylheptan-2-one through the unsaturated ketone compound, so that the yield of the desired product can be greatly improved.

As the dehydration condition, it is preferable to make an acidic substance present in the hydrogenation reaction system as will be described later.

The hydrogenation reaction may be carried out in the presence of a metal catalyst used in usual hydrogenation reaction. For example, such a metal catalyst may include catalysts having palladium, rhodium, nickel or platinum as an active component. The metal catalyst may be used in the form of a metal itself, a metal oxide, or an alloy of the metal with other metal, or in such a form that the metal is supported on a carrier such as activated carbon, alumina, silica gel or kieselguhr. Any of these forms can be applied in this reaction. In particular, the metal catalyst may preferably be used in the form of palladium/carbon, palladium/alumina, or nickel/kieselguhr.

Such a metal catalyst may be used usually in an amount of from 0.01 to 5% by weight based on the weight of the 4-hydroxy-6-methylheptan-2-one-containing condensate. From the viewpoint of practical reaction rate and cost of production, it may preferably be used in an amount of from 0.1 to 1% by weight based on the weight of the 4-hydroxy-6-methylheptan-2-one-containing condensate.

The hydrogenation reaction may preferably be carried out in the presence of an acidic substance as stated above, in order to more enhance the reaction rate to obtain the desired product 6-methylheptan-2-one in a good efficiency and at a high yield. Such an acidic substance may include, e.g., sulfonic acids such as methanesulfonic acid, benzenesulfonic acid and p-toluenesulfonic acid; aliphatic or aromatic carboxylic acids such as acetic acid, propionic acid, octanoic acid, terephthalic acid and phthalic acid; mineral acids such as sulfuric acid and hydrochloric acid; Lewis acids such as tin chloride, titanium chloride and aluminum chloride; heteropoly-acids such as tungstophosphoric acid, tungstosilicic acid and molybdophosphoric acid; and acid type ion-exchange resins such as sulfonic acid type or carboxylic acid type ones.

Any of these acidic substances may be used usually in an amount of from 0.1 to 10 mol % based on the 4-hydroxy-6-methylheptan-2-one-containing condensate. From the viewpoint of practical reaction rate and cost of production, it may preferably be used in an amount of from 0.5 to 2 mol % based on the 4-hydroxy-6-methylheptan-2-one-containing condensate.

Alternatively, the reaction may be carried out using a metal catalyst that carries the active metal such as palladium, rhodium, nickel or platinum on a support having an acidic site, such as silica, alumina or acid type ion-exchange resin. In this case, the use of only such a metal catalyst enables progress of the reaction as in the case where the acidic-substance is used.

The hydrogenation reaction may be carried out within a temperature range of from 80° C. to 170° C. From the viewpoint of reaction rate and selectivity to 6-methylheptan-2-one, it may preferably be carried out within a temperature range of from 90° C. to 130° C.

In the present invention, the hydrogenation reaction is carried out in an atmosphere of hydrogen gas, where the hydrogen gas may be at a pressure, having no particular limitations, preferably within the range of from 1 to 50 atmospheric pressure, and more preferably from 3 to 10 atmospheric pressure. The reaction time for hydrogenation may vary depending on reaction conditions, and may usually be within the range of from 1 hour to 20 hours. For example, when the reaction is carried out at a reaction temperature of 100° C. under a hydrogen gas pressure of 8 kg/cm$^2$, using p-toluenesulfonic acid as the acidic substance in an amount of 1 mol % based on the 4-hydroxy-6-methylheptan-2-one-containing condensate and using palladium/carbon as the metal catalyst in an amount of 0.2% by weight based on the 4-hydroxy-6-methylheptan-2-one-containing condensate, the hydrogenation reaction is completed in 2 hours.

In the hydrogenation reaction, it is not necessarily required to use a solvent. From the viewpoint of the control of reaction, a solvent inert to the hydrogenation reaction may be used. Such a solvent may include, e.g., lower aliphatic alcohols such as methanol, ethanol, propanol, isopropanol, n-butanol, s-butanol and t-butanol; cyclic or acyclic ethers such as tetrahydrofuran, 1,4-dioxane, diethyl ether, diisopropyl ether and di-n-butyl ether; and aliphatic or aromatic hydrocarbons such as hexane, heptane, octane, benzene, toluene and xylene.

The catalyst may be removed by a conventional method, e.g., by the operation of filtration, from the reaction solution obtained as a result of the hydrogenation reaction under a dehydration condition, and thereafter the water formed as a result of the reaction may be optionally removed, followed by purification through distillation under an atmospheric pressure or a reduced pressure, whereby 6-methylheptan-2-one with a high purity can be readily obtained.

As described above, according to the present invention, 6-methylheptan-2-one, which is useful as a material for synthesizing isophytol or as a material for synthesizing fragrances such as tetrahydrolinalool and dihydrogeraniol, can be produced efficiently and in an industrial scale, simply and inexpensively from isovaleral and acetone, which are produced in an industrial scale and available inexpensively.

EXAMPLES

The present invention will be further described below by Examples. The present invention is by no means limited to these Examples.

Example 1

(a) Aldol Condensation of Isovaleral With Acetone

To a tube type reactor set at 50° C. and having a reaction zone with an internal volume of 75.9 ml, a mixture of isovaleral and acetone [isovaleral/acetone=1/6 (in molar ratio)], and an aqueous 5% potassium hydroxide were continuously fed at a rate of 7.36 ml/min for the former and at a rate of 0.16 ml/min for the latter. The reaction mixture coming out of the tube type reactor was neutralized with acetic acid. The reaction time was 10.1 minutes.

At the time when 220 minutes went by, 254.0 g (2.95 mols) of isovaleral, 1,028.2 g (17.7 mols) of acetone and 36.0 g (32 mmols in terms of KOH) of an aqueous 5% potassium hydroxide were fed to obtain 1,310.2 g of a reaction mixture having been neutralized with acetic acid. The reaction mixture thus obtained was analyzed by the internal standard method using gas chromatography [columns: Silicone DC QF-1 (available from Gasukuro Kogyo Inc.); column temperature: 60° C.→200° C. (rate of temperature rise: 5° C./minute); injection temperature: 245° C.; FID detector] to reveal that 295.7 g (yield: 69.5%) of 4-hydroxy-6-methylheptan-2-one and 26.4 g (yield: 7.1%) of 6-methyl-3-hepten-2-one were contained in it. From this reaction mixture, potassium acetate was removed by filtration, and thereafter the filtrate obtained was subjected to simple distillation under reduced pressure of 17 to 20 Torr to collect 359.4 g of a fraction having a boiling point of from 80° to 100° C. Analysis with gas chromatogaphy under the same conditions as the above revealed that 216.2 g (1.50 mols) of 4-hydroxy-6-methylheptan-2-one and 81.2 g (0.64 mol) of 6-methyl-3-hepten-2-one were contained in this fraction.

(b) Synthesis of 6-Methylheptan-2-One

Of the fraction obtained by the above simple distillation, 200.0 g of a portion [containing 120.3 g (0.834 mol) of 4-hydroxy-6-methylheptan-2-one and 45.1 g (0.358 mol) of 6-methyl-3-hepten-2-one] was charged into an autoclave made of glass, having a stirrer and an internal volume of 1,000 ml, and 1.27 g (6.68 mmols) of p-toluenesulfonic acid monohydrate and 0.17 g of a 5%-palladium/carbon catalyst were added thereto in an atmosphere of nitrogen. Thereafter, the inside of the reaction system was replaced by 8 kg/cm$^2$ of hydrogen gas, and the internal temperature was raised to 100° C. Since the absorption of hydrogen began in the course of temperature rise, pressurized hydrogen was fed as necessary in order to maintain the internal pressure.

After the temperature of the reaction solution reached 100° C., the reaction was further carried out for 2.0 hours. From the reaction mixture obtained, the 5%-palladium/carbon catalyst was removed by filtration, and the filtrate obtained was analyzed by the same internal standard method using the gas chromatography as the above, to reveal that 140.17 g (yield: 91.9%) of 6-methylheptan-2-one was contained in it.

From the filtrate thus obtained, the aqueous layer was separated, followed by distillation of the organic layer to obtain 134.5 g of the desired product 6-methylheptan-2-one (boiling point: 83°–85° C./about 50 mmHg).

Example 2

(a) Aldol Condensation of Isovaleral With Acetone

In a three-necked flask made of glass, having a stirrer, a reflux condenser and an internal volume of 300 ml, 26.4 g (0.3 mol) of isovaleral and 104.4 g (1.8 mols) of acetone were charged, and the liquid mixture obtained was heated to 40° C. To the liquid mixture thus heated, 2.4 g (3 mmols) of an aqueous 5% sodium hydroxide was added, followed by stirring. The mixture obtained turned to a colorless, transparent uniform solution through a slightly milky white state, in about 5 minutes after the addition of the aqueous sodium hydroxide, and generated heat at the same time, where its internal temperature rose to 59° C. Thereafter, the internal temperature gradually lowered to bath temperature (40° C.). At this point of time, 30 minutes had passed after the addition of the aqueous 5% sodium hydroxide.

The reaction mixture thus obtained was neutralized with acetic acid, and thereafter the salt formed (sodium acetate) was removed by filtration to obtain 129.7 g of a filtrate. The filtrate obtained was analyzed by the same internal standard method using the gas chromatography as in Example 1, to reveal that 30.33 g (yield: 70.1%) of 4-hydroxy-6-methylheptan-2-one and 3.97 g (yield: 10.5%) of 6-methyl-3-hepten-2-one were contained in it. The filtrate obtained in the above was subjected to simple distillation in the same manner as in Example 1 to obtain 37.6 g of a simple distillation fraction (boiling point: 80°–100° C./17–20 Torr) containing 24.8 g (0.172 mol) of 4-hydroxy-6-methylheptan-2-one and 7.2 g (0.057 mol) of 6-methyl-3-hepten-2-one.

(b) Synthesis of 6-Methylheptan-2-One 37.6 g of the fraction obtained by the above simple distillation was charged into an autoclave made of glass, having a stirrer and an internal volume of 100 ml, and 0.33 g (1.72 mmols) of p-toluenesulfonic acid monohydrate and 32 mg of a 5%-palladium/carbon catalyst were added thereto in an atmosphere of nitrogen. Thereafter, the inside of the reaction system was replaced by 8 kg/cm² of hydrogen gas, and the internal temperature was raised to 100° C. In the same manner as the step (b) in Example 1, after the temperature of the reaction solution reached 100° C., the reaction was further carried out for 3 hours. From the reaction mixture obtained, the 5%-palladium/carbon catalyst was removed by filtration, and the filtrate obtained was analyzed by the same internal standard method using the gas chromatography as in Example 1, to reveal that 27.0 g (yield: 92%) of 6-methylheptan-2-one was contained in it.

From the filtrate thus obtained, the aqueous layer was separated, followed by distillation of the organic layer to obtain 25 g of the desired product 6-methylheptan-2-one (boiling point: 83°–85° C./about 50 mmHg).

Example 3

(a) Aldol Condensation of Isovaleral With Acetone

Aldol condensation was carried out in the same manner as in Example 2 except that the aqueous 5% sodium hydroxide was replaced with 0.94 g (3 mmols) of barium hydroxide octahydrate. After 2 hours from the start of the reaction, the catalyst (barium hydroxide) was removed by filtration, and the filtrate obtained was analyzed by gas chromatography in the same manner as in Example 1, to reveal that 26.30 g (yield: 60.8%) of 4-hydroxy-6-methylheptan-2-one and 7.04 g (yield: 18.6%) of 6-methyl-3-hepten-2-one were contained in it.

The filtrate thus obtained was subjected to simple distillation in the same manner as in Example 1 to obtain 37.8 g of a simple distillation fraction (boiling point: 80°–100° C./17–20 Torr) containing 22.8 g (0.158 mol) of 4-hydroxy-6-methylheptan-2-one and 8.6 g (0.068 mol) of 6-methyl-3-hepten-2-one.

(b) Synthesis of 6-Methylheptan-2-One 37.8 g of the fraction obtained by the above simple distillation was charged into an autoclave made of glass, having a stirrer and an internal volume of 100 ml, and 0.3 g (1.58 mmols) of p-toluenesulfonic acid monohydrate and 31.4 mg of a 5%-palladium/carbon catalyst were added in an atmosphere of nitrogen. Thereafter, the inside of the reaction system was replaced by 8 kg/cm² of hydrogen gas, and the internal temperature was raised to 100° C. In the same manner as the step (b) in Example 1, after the temperature of the reaction solution reached 100° C., the reaction was further carried out for 3 hours. From the reaction mixture obtained, the 5%-palladium/carbon catalyst was removed by filtration, and the filtrate obtained was analyzed by the same internal standard method using the gas chromatography as in Example 1, to reveal that 26.3 g (yield: 91%) of 6-methylheptan-2-one was contained in it.

From the filtrate thus obtained, the aqueous layer was separated, followed by distillation of the organic layer to obtain 24.6 g of the desired product 6-methylheptan-2-one (boiling point: 82°–83° C./about 50 mmHg).

INDUSTRIAL UTILIZATION

The production process of the present invention is useful as a process for producing in an industrial scale 6-methylheptan-2-one, useful as a material for synthesizing isophytol or as a material for synthesizing fragrances such as tetrahydrolinalool.

We claim:

1. A process for producing 6-methylheptan-2-one, comprising subjecting isovaleral and acetone to aldol condensation in the presence of a basic substance to form a condensate which contains 4-hydroxy-6-methylheptan-2-one, and subjecting the condensate to hydrogenation reaction under a dehydration condition.

2. The process according to claim 1, wherein said isovaleral and acetone are in a molar ratio of from 1/5 to 1/8.

3. The process according to claim 1, wherein said basic substance is at least one compound selected from the group consisting of an alkali metal hydroxide and an alkaline-earth metal hydroxide.

4. The process according to claim 1, wherein said basic substance is at least one compound selected from the group consisting of a metal alkoxide and a metal amide.

5. The process according to claim 1, wherein said basic substance is used in an amount of from 0.5 to 5 mol % based on the isovaleral.

6. The process according to claim 1, wherein said hydrogenation reaction is carried out in the presence of a hydrogenation catalyst.

7. The process according to claim 6, wherein said hydrogenation catalyst is palladium/carbon, palladium/alumina, or nickel/kieselguhr.

8. The process according to claim 6, wherein said hydrogenation catalyst is used in an amount of from 0.1 to 1% by weight based on the condensate which contains 4-hydroxy-6-methylheptan-2-one.

9. The process according to claim 6, wherein said hydrogenation reaction is carried out at a hydrogen gas pressure of from 1 to 50 atmospheric pressure.

10. The process according to claim 1, wherein said hydrogenation reaction is carried out in the presence of an acidic substance.

11. The process according to claim 10, wherein said acidic substance is at least one selected from the group consisting of a sulfonic acid, an aliphatic or aromatic carboxylic acid, a mineral acid, a Lewis acid, a heteropoly-acid and an acid type ion-exchange resin.

12. The process according to claim 11, wherein said acidic substance is used in an amount of from 0.5 to 2 mol % based on the condensate which contains 4-hydroxy-6,-methylheptan-2-one.

* * * * *